United States Patent [19]
Kirpotin

[11] Patent Number: 6,110,491
[45] Date of Patent: *Aug. 29, 2000

[54] COMPOUND-LOADED LIPOSOMES AND METHODS FOR THEIR PREPARATION

[75] Inventor: Dmitri Kirpotin, San Francisco, Calif.

[73] Assignee: Hermes Biosciences, Inc., San Francisco, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/953,808

[22] Filed: Oct. 21, 1997

Related U.S. Application Data

[60] Provisional application No. 60/028,931, Oct. 22, 1996.

[51] Int. Cl.$^7$ .................................................. A61K 9/127
[52] U.S. Cl. ............................ 424/450; 264/4.1; 264/4.3
[58] Field of Search ...................... 426/450, 1.21, 426/9.321, 9.51, 417, 94.3; 428/402.2; 935/54; 264/4.1, 4.3, 4.6

[56] References Cited

U.S. PATENT DOCUMENTS 4,946,683  8/1990  Forssen ................................. 424/422

OTHER PUBLICATIONS

Haran et al., 1151 *Biochimica et Biophysica Acta.* 201 (1993).
Bally, M., et al., *Biochim. Biophys. Acta* 812:66–76 (1985).
Barenholz, C., and Haran, G., *Chem. Abstr.* 114: 12199g (1988).
Carmichael, et al., *Cancer Res.* 47:936–942 (1987).
Gabizon, A., et al., *J. Liposome Res.* 1:123–135 (1988–89).
Haran, G., et al., *Biochim. Biophys. Acta* 1151:201–215 (1993).
Lasic, D.D., et al., *Biochim. Biophys. Acta* 1239: 145–156 (1995).
Lasic, DD, *Liposomes: From Physics to Applications* 315–317 (Elsevier 1993).
Maier, et al., *Chem. Phys. Lipids* 40:333–345 (1986).
Mayer, et al., *Biochim. Biophys. Acta* 816:294–302 (1985).
Mayer, et al., *Biochim. Biophys. Acta* 857:123–126 (1986).
Nichols and Deamer, D., *Biochim. Biophys. Acta* 455:269–171 (1976).
Schwendener, *Cancer Drug Delivery* 3:123–129 (1986).
Schwendener, et al., *Onkologie* 10:232–239 (1987).
Straubinger, R.M., et al., *Biochemistry* 29:4929–4939 (1990).
Szoka, F.C., Jr., and Papahadjopoulos, D., *Proc. Natl. Acad. Sci. USA* 75:4194–4198 (1978).
Zhu, et al., 39 *Cancer Chemother Pharmacol* 138 (1996).

*Primary Examiner*—Gollamudi S. Kishore
*Attorney, Agent, or Firm*—Kristine H. Johnson; Macheledt Bales & Johnson LLP

[57] ABSTRACT

A liposome composition containing encapsulated compound in stable precipitated form, and a method for producing the composition, are disclosed. The concentration of precipitated compound within the liposomes is severalfold higher than that in the bulk medium, and the concentration of compound within the liposomes is not reduced in the presence of a proton or alkali metal-ion ionophore added to the suspension.

24 Claims, 1 Drawing Sheet

Fig. 1

COMPOUND-LOADED LIPOSOMES AND METHODS FOR THEIR PREPARATION

This application claims benefit of U.S. Provisional Patent Application No. 60/028,931, filed on Oct. 22, 1996.

FIELD OF THE INVENTION

The present invention relates to liposomes loaded with compounds in precipitated form, and to methods of producing such liposomes.

REFERENCES

Bally, M., et al., *Biochim. Biophys. Acta* 812:66–76 (1985).
Barenholz, C., and Haran, G., *Chem. Abstr.* 114: 12199g (1988).
Carmichael, et al., *Cancer Res.* 47:936–942 (1987).
Gabizon, A., et al., *J. Liposome Res.* 1:123–135 (1988–89).
Haran, G., et al., *Biochim. Biophys. Acta* 1151:201–215 (1993).
Lasic, D. D., et al., *Biochim. Biophys. Acta* 1239: 145–156 (1995).
Lasic, D D, *Liposomes: From Physics to Applications* 315–317 (1993)
Maier, et al., *Chem. Phys. Lipids* 40:333–345 (1986).
Mayer, et al., *Biochim. Biophys. Acta* 816:294–302 (1985).
Mayer, et al., *Biochim. Biophys. Acta* 857:123–126 (1986).
Nichols and Deamer, D., *Biochim. Biophys. Acta* 455:269–171 (1976).
Schwendener, *Cancer Drug Delivery* 3:123–129 (1986).
Schwendener, et al., *Onkologie* 10:232–239 (1987).
Straubinger, R. M., et al., *Biochemistry* 29:4929–4939 (1990).
Szoka, F. C., Jr., and Papahadjopoulos, D., *Proc. Natl. Acad. Sci. USA* 75:4194–4198 (1978).

BACKGROUND OF THE INVENTION

Liposomes, or lipid bilayer vesicles, have been used or proposed for use in a variety of diagnostic and therapeutic applications. Particularly in their use as carriers in vivo of diagnostic or therapeutic compounds, the liposomes are typically prepared to contain the compound in liposome-entrapped form.

Ideally, such liposomes can be prepared to include the entrapped compound (i) with high loading efficiency, (ii) at a high concentration of entrapped compound, and (iii) in a stable form, i.e., with little compound leakage on storage.

Methods for forming liposomes under conditions in which the compound to be entrapped is passively loaded into the liposomes are well known. Typically, a dried lipid film is hydrated with an aqueous phase medium, to form multi-lamellar vesicles which passively entrap compound during liposome formation. The compound may be either a lipophilic compound included in the dried lipid film, or a water-soluble compound contained in the hydrating medium. For water-soluble compounds, this method gives rather poor encapsulation efficiencies, in which typically only 5–20% of the total compound in the final liposome suspension is in encapsulated form. Additional compound may be lost if the vesicles are further processed, i.e., by extrusion, to produce smaller, more uniformly sized liposomes. The poor encapsulation efficiency limits the amount of compound that can be loaded into the liposomes, and can present costly compound-recovery costs in manufacturing.

A variety of other passive entrapment methods for forming compound-loaded liposomes, including solvent injection methods and a reverse-evaporation phase approach (Szoka and Papahadjopoulos, 1978) have been proposed. These methods tend to suffer from relatively poor loading efficiencies and/or difficult solvent handling problems.

It has also been proposed to passively load compounds into liposomes by incubating the compound with preformed liposomes at an elevated temperature at which the compound is relatively soluble, allowing the compound to equilibrate into the liposomes at this temperature, then lowering the temperature of the liposomes to precipitate compound within the liposomes. This method is limited by the relatively poor encapsulation efficiencies which are characteristic of passive loading methods. Also, the compound may be quickly lost from the liposomes at elevated temperature, e.g., body temperature.

Compound loading against an inside-to-outside pH or electrochemical liposome gradient has proven useful for loading ionizable compounds into liposomes. In theory, very high loading efficiencies can be achieved by employing suitable gradients, e.g., pH gradients of 2–4 units, and by proper selection of initial loading conditions (Nichols and Deamer, 1976). With this method, compound leakage from the liposomes will follow the loss of ion gradient from the liposomes. Therefore, compound can be stably retained in liposome-encapsulated form only as long as the ion gradient is maintained.

This gradient stability problem was addressed, and at least partially solved, by employing an ammonium salt gradient for compound loading (Haran, et al., 1993). Here excess ammonium ions, which act as a source of protons in the liposomes, function in addition as a battery to replenish protons lost during storage, thus increasing the lifetime of the proton gradient, and therefore reducing the rate of leakage from the liposomes. The method is limited to ionizable amine compounds.

Lastly, the utility of precipitation for liposome loading was hypothesized in the literature. Lasic D. D. (1993).

SUMMARY OF THE INVENTION

The invention includes a liposome composition comprising a suspension of liposomes contained in an aqueous bulk-phase medium; the liposomes comprising a coprecipitate of an ionizable compound and a charged precipitating agent, where the concentrations of both the compound and the precipitating agent within the liposomes are severalfold higher than the compound and precipitating agent concentrations in the bulk-phase medium, respectively, and the concentration of compound within the liposomes is not reduced by the presence in the suspension of a proton or alkali metal-ion ionophore. A composition as above, wherein the bulk phase medium is substantially free of the precipitating agent is preferred.

In one aspect of the above, the invention includes, a suspension of liposomes contained in an aqueous bulk-phase medium, and an ionizable compound contained within the liposomes in the form of a coprecipitate with a charged, polyionic polymer which serves as the precipitating agent. The concentrations of both the compound and the polymer within the liposomes are severalfold higher than the compound and the polymer concentrations in the bulk-phase medium, respectively, and the concentration of compound within the liposomes is substantially unaffected by the addition to the suspension of a proton or alkali metal-ion ionophore. The bulk phase medium may be substantially free of the precipitating agent.

In one general embodiment, the polymer is a polysulfate, polysulfonate, polyphosphate, or polycarboxylate polymer, and, preferrably, the compound is ionizable by protonation to a positively charged form. An exemplary composition includes doxorubicin, or analog thereof, in combination with polyacrylate, chondroitin sulfate A, polyvinylsulfuric acid, or polyphosphoric acid.

In another general embodiment, the polymer is a polymeric base, and, preferrably, the compound is ionizable by deprotonation to a negatively charged form.

In another aspect, the invention includes a liposome composition comprising a suspension of liposomes contained in an aqueous bulk-phase medium, and an ionizable compound contained within the liposomes in the form of a pH-induced precipitate. The concentration of the compound within the liposomes is severalfold higher than that in the bulk-phase medium, and the concentration of compound within the liposomes is not reduced by the presence in the suspension of a proton or alkali metal-ion ionophore.

Also forming part of the invention is a method of producing a suspension of liposomes having an ionizable compound stably encapsulated in the liposomes in precipitated form. The method comprises adding a compound to be encapsulated to a suspension of liposomes in bulk-phase aqueous medium, the liposomes having substantially no outside to inside pH or electrochemical ion gradient and containing charged precipitating agent of higher inside/lower outside concentration, and the precipitating agent being oppositely charged to the compound; and incubating under conditions that allow active uptake of the compounds by the precipitating agent. In this method, the absence is in reference to the ion having the same charge sign as the compound to be loaded.

In one embodiment, is a method which includes adding the compound to a dispersion of liposomes contained in a bulk-phase aqueous medium, where the liposomes have a higher-inside/lower-outside gradient of a charged, polyionic polymer which can serve as the counterion of the compound. The compound-containing dispersion is then incubated under conditions that allow uptake of the compound by the liposomes to a compound concentration that is severalfold that of the compound concentration in the bulk-phase medium, as evidenced by the formation of a precipitate inside the liposomes.

The incubating step may be carried out at a temperature above the phase transition temperature of lipids forming the liposomes. The method may further include removing unprecipitated compound from the bulk phase of the suspension, after compound loading.

In one general embodiment, the polymer is a polysulfate, polysulfonate, polyphosphate, or polycarboxylate polymer, and the compound is ionizable by protonation to a positively charged form, as above. In an exemplary method, the compound is doxorubicin, or an analog thereof, and the polymer is polyacrylate, chondroitin sulfate A, polyvinylsulfuric acid, or polyphosphoric acid.

In still another aspect, the invention includes a method of producing a suspension of liposomes having an ionizable compound stably encapsulated in the liposomes in precipitated form, where the compound is relatively water insoluble at a first pH, and relatively water soluble at a second pH. The method includes adding the compound to a dispersion of liposomes contained in a bulk-phase aqueous medium, where the dispersion has an inside-to-outside liposome pH gradient corresponding to said first and second pH, respectively. The compound and dispersion are incubated under conditions which allow uptake of the compound by the liposomes to a compound concentration that is severalfold that of the compound concentration in the bulk-phase medium, as evidenced by the formation of a precipitate inside the liposomes.

In one embodiment, the inside-to-outside pH gradient may be opposite to that required for loading the same compound in soluble form into liposomes. The method may further include adjusting the pH of the bulk phase medium to that of the internal liposome pH following the incubating step.

In a final aspect, the invention includes a method of producing a suspension of liposomes having an ionizable compound stably encapsulated in the liposomes in precipitated form. The method includes adding the compound to a dispersion of liposomes contained in a bulk-phase aqueous medium, where the liposomes have (i) a higher inside/lower outside gradient of a multivalent, charged precipitating agent, and (ii) substantially no inside-to-outside pH gradient. The compound and dispersion are then incubated under conditions that allow uptake of the compound by the liposomes to a compound concentration that is severalfold that of the compound concentration in the bulk-phase medium, as evidenced by the formation of a precipitate inside the liposomes.

In one general embodiment, the compound, when ionized, has a net positive charge, and the precipitating agent is a multivalent acid. The multivalent acid may be a polymer or non-polymer, organic or inorganic. For instance only, the multivalent acid may be a polysulfate, polysulfonate, polyphosphate or polycarboxylate. In an exemplary method, the compound is doxorubicin, or an analog thereof, and the precipitating agent is tartrate, citrate, sulfate, phosphate, diethylene thiamine pentacetate, or polyacrylate. is polyacrylate, chondroitin sulfate A, polyvinylsulfuric acid, or polyphosphoric acid. In other words, in this embodiment, the precipitating agent may be polymeric or non-polymeric. The polymeric compounds may be, for example, polyacrylate, chondroitin sulfate A, polyvinyl sulfuric acid, or polyphosphoric acid.

In another general embodiment, the compound, when ionized, has a net negative charge, and the precipitating agent is a multivalent organic base. The multivalent organic base may be polymeric or non-polymeric. In an exemplary method, the compound is penicillin, and the organic base is benzathine.

These and other objects and features of the invention will become more fully apparent from the following detailed description of the invention is read in conjunction with the accompanying drawing.

DETAILED DESCRIPTION OF THE INVENTION

I. Liposome Composition with Precipitated Compound

This section describes a novel liposome composition containing liposomes suspended in a bulk-phase aqueous medium, and an ionizable compound contained within the liposomes in the form of a stable precipitate, at a concentration of compound that is several times that of the compound in the bulk-phase medium.

A. Charged-Polymer Precipitating Agent

In one general aspect, the compound entrapped in precipitated form is ionizable to a charged form, and the precipitating agent is a charged polymer which serves as the counterion of the compound. That is, the compound in ionized form has a net positive or negative charge, and the polymer charged groups have the opposite charge.

As the term is used herein, "polymers" refers to molecules consisting of repetitive units of preferably similar chemical structure, with molecular weights, roughly defined, from 400 to 2,000,000, soluble in water, and containing in their structure ionizable groups, that is, chemical functional groups capable of electrolytic dissociation resulting in the formation of ionic charge. The following are examples of such suitable polymers for use in the invention.

1. Acidic and basic polysaccharides, both natural and natural-derived, including: polygalacturonates, hyaluronic acid, gum arabic, chondroitin sulfates A, B, and C, keratin sulfates, dermatan sulfates, heparin and its derivatives, pectin and its derivatives, alginic (poly-anhydromannuronic) acid, teichoic acids, chitosans; derivatives of cellulose, amylose, amylopectin, dextran, or other neutral polysaccharide obtained by introduction of carboxyalkyl, phosphate, sulphate, amino-, mono-, di-, trialkylamino, tetraalkylammonium functional groups, derivatives of the said polysaccharides with nitrogen heterocycles, and derivatives obtained by grafting other ionizable functions to polysaccharide backbone.

2. Acidic and basic polypeptides and proteins, synthetic or natural: polymers and copolymers containing glutamic acid, aspartic acid, lysine, arginine, ornithine, other non-protein amino acids with ionizable function in the side chain, proteins with extremely high or low isoelectric points, such as cytochrome C, histone, protamine, trypsin, and partially hydrolyzed collagens.

3. Nucleic acids, oligo- and polynucleotides, and their derivatives.

4. Polymeric carboxylic acids: polymers and copolymers containing units of acrylic acid, methacrylic acid, maleic acid, proparglycic acid, styrenecarboxylic acid, or other alkenyl- or alkenylarylcarboxylic acid; polymers and copolymers containing ionizable carboxyls in side groups on a polyamide, polyether, polyester, or polycyclic backbone.

5. Polymers with phosphate groups in the polymer backbone, such as polyphosphates, or in side chains, such as polyvinylphosphate.

6. Polymers bearing sulfo groups, such as: polyvinylsulfate, polyvinylsulfonate, polystyrenesulfonate, sulfated rosin gum (naphtenate).

7. Polymeric amines and amino containing heterocycles, whether in side groups or in the polymer backbone, such as: polyvinlyamines, polyallylamines, polyvinlalkylamines and polyvilyltrialkylammonium salts, polyvinylpyridines, quaternized polyvinylpyridines, poly(alkylaminoalkyl)acrylates, poly(aminoalkyl)vinyl alcohols, and copolymers containing the units of the above polymers.

8. Polymers containing thiocarboxylic, dithiocarboxylic, thiosulfate, and thiophosphate functions in side chains or in the main polymer backbone.

Compounds which are suitable in this embodiment are ionizable compounds whose solubility depends upon the presence of unneutralized charged groups. They are exemplified by the following pharmaceutical substances: antihistamine ethylenediamine derivatives (bromphenifamine, diphenhydramine); Anti-protozoal: quinolones (iodoquinol); amidines (pentamidine); antihelmintics (pyrantel); antischistosomal drugs (oxaminiquine); antifungal triazole derivatives (fliconazole, itraconazole, ketoconazole, miconazole); antimicrobial cephalosporins (cefazolin, cefonicid, cefotaxime, ceftazimide, cefuoxime); antimicrobial beta-lactam derivatives (aztreopam, cefmetazole, cefoxitin); antimicrobials of erythromycine group (erythromycin, azithromycin, clarithromycin, oleandomycin); penicillins (benzylpenicillin, phenoxymethylpenicillin, cloxacillin, methicillin, nafcillin, oxacillin, carbenicillin); tetracyclines (precipitate in the presence of $Mg^{2+}$ and $Zn^{2+}$; other antimicrobial antibiotics, novobiocin, spectinomycin, vancomycin; antimycobacterial drugs: aminosalicyclc acid, capreomycin, ethambutol, isoniazid, pyrazinamide, rifabutin, rifampin, clofazime; antiviral adamantanes: amantadine, rimantadine; quinidine derivatives: chloroquine, hydroxychloroquine, promaquine, qionone; antimicrobial qionolones: ciprofloxacin, enoxacin, lomefloxacin, nalidixic acid, norfloxacin, ofloxacin; sulfonamides; urinary tract antimicrobials: methenamine, nitrofurantoin, trimetoprim; nitroimidazoles: metronidazole; antineoplastic drugs: bleomycin, nitrogen mustards (chlorambucil, melphalan), nitrous bases and nucleoside analogs (cytarabine, dacarbazime, fludarabine, fluorouracil, mercaptopurine, thioguanine, procarbazine); anthracyclines (doxorubicin, daunorubicin), antifolates (methotrexate), vinca derivatives (vincristine, vinblastine, vinorelbine), steroid derivatives (tamoxifen), ionic taxane derivatives; cholinergic quaternary ammonium compounds (ambethinium, neostigmine, physostigmine); anti-Alzheimer aminoacridines (tacrine); anti-Parkinsonal drugs (benztropine, biperiden, procyclidine, trihexylhenidyl); anti-muscarinic agents (atropine, hyoscyamine, scopolamine, propantheline); adrenergic dopamines (albuterol, dobutamine, ephedrine, epinephrine, norepinephrine, isoproterenol, metaproperenol, salmetrol, terbutaline); ergotamine derivatives; myorelaxants or curane series; central action myorelaxants; baclophen, cyclobenzepine, dentrolene; nicotine; beta-adrenoblockers (acebutil, amiodarone); benzodiazepines (ditiazem); antiarrythmic drugs (diisopyramide, encaidine, local anesthetic series—procaine, procainamide, lidocaine, flecaimide), quinidine; ACE inhibitors: captopril, enelaprilat, fosinoprol, quinapril, ramipril; antilipidemics: fluvastatin, gemfibrosil, HMG-coA inhibitors (pravastatin); hypotensive drugs: clonidine, guanabenz, prazocin, guanethidine, granadril, hydralazine; and non-coronary vasodilators: dipyridamole.

An exemplary composition which employs a charged polymeric precipitating agent is described in Example 1, and includes the compound doxorubicin coprecipitated with polyacrylic acid. Example 3 describes a composition having the same compound, but precipitated with chondroitin sulfate A. Example 4 describes a similar drug composition, but precipitated with a polyvinylsulfuric acid polymer or a polyphosphoric acid polymer.

The selection of other suitable, co-precipitating ionizable compound/charged precipitating agent pairs is discussed in Section II below. At this point, it is noted only that the pair must exist in oppositely charged forms at a selected pH, preferably between about pH 4.5 and 9, more preferably in the pH range 6–8.

The concentration of precipitating agent inside the liposomes is preferably such that the concentration of charged groups, e.g., carboxyl, sulfate, or amine groups, is greater than the concentration of co-precipitated compound. In a composition having a final drug concentration of 100 mM, for example, the internal compound concentration of the polymer charge groups will typically be at least this great According to another aspect of the invention, the charged precipitating agent is present at a high-internal/low-external concentration; that is, there is a concentration gradient of agent across the liposome membranes in the composition. If the precipitating agent is present in significant amounts in the bulk phase, the agent can serve as a sink for liposome-entrapped precipitated compound, thus drawing off the compound over time. Preferably, the liposomes are prepared, as described in Section II below, so that the composition is substantially free of precipitating agent in the bulk phase (outside aqueous phase).

Figure 1:
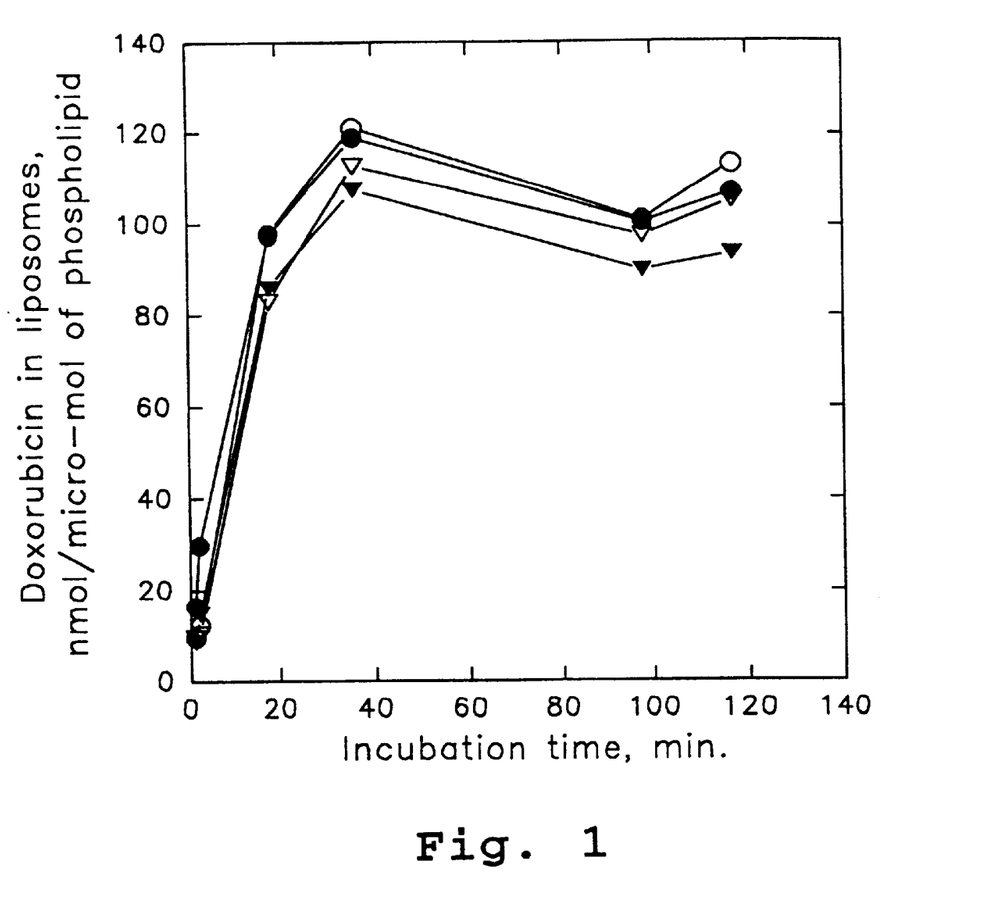
FIG. 1 is a plot showing doxorubicin concentration in liposomes as a function of liposome/drug incubation time for liposomes loaded in the absence of a membrane-active ion carrier (•) and in the presence of valinomycin (•), CCCP (∇) or nigericin (▽).

One unexpected feature of the invention is that the compound concentration in the liposomes is not reduced in the presence in the suspension of a proton or alkali metal-ion ionophore, that is, an ionophore that has the ability to selectively promote proton or alkali metal-ion transport across a lipid bilayer membrane, when the ionophore is added to preformed liposomes. One explanation to this phenomenon is that the ionophore has no significant effect on the transport of the charged precipitating agents across the liposome bilayer membrane. Another explanation is that, in contrast to pH- or ammonium-ion gradient loading methods (Haran, et al., 1993; Mayer et al., 1985, 1986), the loading of a compound does not require maintaining of a transmembrane pH-, ammonium ion-, or other electrochemical ion gradient, as shown by Examples 7–9 below. This feature is illustrated in FIG. 1, where liposomes having an entrapped polyionic polymer (potassium polyacrylate) were loaded with doxorubicin in the presence of an ionophore, carbonyl cyanide m-chlorophenol hydrazone (CCCP, (▽), valinomycin (•) or nigericin (▽). (Example 6). CCCP is specific to hydrogen protons, valinomycin is specific to potassium and hydrogen protons, and nigericin is specific to sodium, potassium and hydrogen protons. As seen in the figure, loading of doxorubicin was substantially unaffected by the presence of such ionophores, when compared to loading in the absence of an ionophore (•).

Precipitation of drug within the liposome can be achieved by incorporation of non-charged polymers, in addition to charged, polyionic polymers discussed above. For example, polyvinyl pyrrilodone can be used to form a stable precipitate with a drug, where the precipitate is stabilized by hydrogen or van der Waals interactions between the polymer and the drug. Polyvinyl pyrrilodone is capable of forming coprecipitates with, for example, the anticoagulant warfarin and the antiinflammatory oxybutazone.

B. pH-Precipitated Compound

In another general aspect, the composition contains, as the liposome-entrapped compound, an ionizable compound that is in the form of a pH-induced precipitate.

Similar to the composition described in subsection A, the concentration of the compound within the liposomes in the present composition is several times higher than that in the bulk-phase medium, and the concentration of compound within the liposomes is substantially unaffected by the addition to the suspension of a proton or alkali metal-ion ionophore. Unlike the first-described composition, the retention of precipitated drug is not dependent on the maintenance of a gradient of precipitating agent. In fact, it may be desired to adjust the bulk-phase suspension to the pH at or near the internal pH at which the compound is precipitated.

Compounds suitable for use in the invention are those which have relatively low water solubility at a first pH, preferably in the pH range 3–9, and relatively high water solubility at a second pH, also preferably in the same pH range. Typically, the water solubility of compound at the second pH will be at least 10 times, and preferably 25–100 times or more, the water solubility of the compound at the first pH. Examples of suitable compounds include the following pharmaceutical compounds (solubility data are from *AHFS DRUG REGISTER*, 1996):

Cefalosporines (cefixime, cephalexin); tetracycline (solubility in water at acidic pH, 100 mg/ml; at neutral pH, 0.4 mg/ml); rifampin; acyclovir, gancyclovir (solubility in water at alkaline pH, >100 mg/ml; at pH 7.4, 2.5 mg/ml); quinolones: ciprofloaxacin, enoxacin, nalidixic acid, norfloxacin, ofloxacin; norfloxacin having the following pH-dependent solubilities at 37° C.:

| pH <5.5 | >40 mg/ml |
| pH 6.5 | 2.8 mg/ml |
| pH 7.0 | 1.5 mg/ml |
| pH 8.0 | 1.9 mg/ml | and ofloxacin, having the following pH dependent solubilities at room temperature:

| pH 2.5 | 60 mg/ml |
| pH 7 | 4 mg/ml |
| pH 9.8 | 303 mg/ml | antitumor nitrogen mustard derivatives: melphalane; antiesterogens: tamoxifen; nitrous base analogs: thioguanine, mercaptopurine; dihydropyridine cardiovascular drugs: nicardipine, amlodipine, nifedipine, amrinone, whose pH dependent solubility is:

| pH 4.1 | 25 mg/ml |
| pH 6 | 0.9 mg/ml |
| pH 8 | 0.9 mg/ml | non-steroid antiinflammatory agents: ibuprofen (soluble at alkaline pH, poorly soluble at neutral pH); HIV protease inhibitors: indinavir, ritonavir, and saquinavir.

The internal pH of the liposomes in the composition is preferably at or near the minimum-solubility pH of the precipitated compound, or at a lower pH of 4 to 5.5 or an upper pH of 8.5 to 10. As indicated above, the bulk phase pH may be adjusted to the internal pH, eliminating any transmembrane pH in the composition, particularly if necessary to bring the bulk phase pH within the range pH 6–8 suitable for parenteral use.

The liposome compositions of the invention are useful in a variety of diagnostics and therapeutic applications well known to those skilled in the art III. Preparing Liposome Compositions In another general aspect, the invention includes a method of producing a suspension of liposomes having an ionizable compound stably encapsulated in the liposomes in precipitated form, at a concentration of compound that is several times that of the compound in the bulk-phase medium.

A. Compound Loading by Charged Polymer

This method is useful in producing the liposome composition described in Section IA above. In practicing the method, liposomes are prepared to include an encapsulated charged polymer, such as listed in Section IA above. The polymer used in the method will be one capable of precipitating the selected compound to be entrapped, and the polymer concentration will preferably be greater, in terms of charge-group concentration, than the final desired concentration of precipitated drug. (As used herein, "compound concentration" refers to the total amount of drug, in both solute and precipitate form, in a given volume. Thus, for a compound in liposome-encapsulated form, the concentration of compound in the liposomes is determined from the total amount of compound contained in the liposomes divided by the total internal volume of the liposomes in the suspension, as calculated for example, from the total lipid concentration of the suspension.

Thus, for example, if the desired final concentration of compound in the liposomes is 100 mM, a final polymer concentration providing at least 100 mM in polymer charge groups should be selected. To identify a suitable polymer, various polymers taken for example from the list above are made up to the desired concentration, at a selected pH typically around 6–8, and the selected compound is added to a concentration corresponding to the desired liposome-entrapped concentration. If a strong precipitation is observed, after a suitable incubation time, the polymer is suitable for that compound in the present method.

Liposomes having a higher-inside/lower-outside gradient of a charged, polyionic polymer are formed by preparing an aqueous polymer solution, using a polyionic polymer, selected as described above and at a concentration determined as described above. It is preferred that the polymer solution have a viscosity suitable for lipid hydration, described below. The pH of the aqueous polymer solution is preferably such that the polymer is in charged form, and preferably the solution has a pH of between about 3–9, more preferably between about 5–8.

The aqueous polymer solution is used for hydration of a dried lipid film, prepared from conventional vesicle-forming lipids, including synthetic vesicle-forming lipids and naturally-occurring vesicle-forming lipids. Exemplary vesicle-forming lipids include the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and have varying degrees of unsaturation. These lipids can be obtained commercially or prepared according to published methods. Other suitable lipids include glycolipids and sterols such as cholesterol. The vesicle-forming lipid can be neutral or charged.

The fluidity or rigidity of the liposome can be controlled to a certain extent by the vesicle-forming lipid used in forming the liposomes. Liposomes fluidity or rigidity affects the rate of release of the entrapped drug in the liposome, and, in some cases it may be preferred to form liposomes having a more fluid nature to enhance release of the precipitated drug from the liposome.

Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature.

A dried lipid film is prepared by dissolving the selected lipids in a suitable solvent, typically a volatile organic solvent, and evaporating the solvent to leave a dried film. The lipid film is hydrated with the aqueous polymer solution to form liposomes.

Example 1 describes preparation liposomes composed of the lipids egg phosphatidycholine (PC), cholesterol (CHOL) and polyethylene glycol derivatized distearolphosphatidyl ethanolamine (PEG-DSPE). The lipids, at a molar ratio of 10:5:1 PC:CHOL:PEG-DSPE were dissolved in chloroform and the solvent was evaporated to form a lipid film. The lipid film was hydrated with an aqueous solution of sodium polyacrylate, to form liposomes having a higher-inside/lower-outside gradient of a charged, polyionic polymer.

Liposomes are then sized to the desired size range, typically between 0.03–1 micron, preferably between 0.03 to 0.5 microns. A standard sizing method involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less.

After sizing, unencapsulated bulk phase polymer is removed by a suitable technique, such as dialysis, centrifugation, size exclusion chromatography or ion exchange to achieve a suspension of liposomes having a high concentration of polymer inside and preferably little to no polymer outside.

The compound to be entrapped is then added to the liposome dispersion for active loading into the liposomes. The amount of compound added may be determined from the total amount of drug to be encapsulated, assuming 100% encapsulation efficiency, i.e., where all of the added compound is eventually loaded into liposomes in the form of precipitate.

The mixture of the compound and liposome dispersion are incubated under conditions that allow uptake of the compound by the liposomes to a compound concentration that is several times that of the compound in the bulk medium, as evidence by the formation of precipitate in the liposomes. The latter may be confirmed, for example, by standard electron microscopy or x-ray diffraction techniques.

Typically, the incubating is carried out at an elevated temperature, and preferably above the phase transition temperature $T_p$ of the liposome lipids. For high-phase transition lipids having a $T_p$ of 50° C., for example, incubation may be carried out at between 55–60° C. The incubation time may vary from between an hour or less to up to 12 hours or more, depending on incubation temperature and the rate of permeation of the compound through the liposome membrane.

At the end of this incubation step, the suspension may be further treated to remove free (non-encapsulated) compound, e.g., using any of the methods mentioned above for removing free polymer from the initial liposome dispersion containing entrapped polymer.

B. Compound Loading by pH Precipitation

This method is useful in preparing the composition described in Section IB above, where the compound is relatively water insoluble at a first pH, and relatively water soluble at a second pH.

In practicing the method, the compound is added to a dispersion of liposomes having an inside-to-outside liposome pH gradient corresponding to the first and second pH, respectively. Specifically, the internal liposome pH is one at which the compound precipitates at low compound concentration, and the bulk phase pH is one at which the compound is relatively soluble. Exemplary compound solubilities for a variety of compounds suitable in the invention are given in Section IB above.

Liposomes are prepared to have an internal aqueous phase at a first pH where the compound to be loaded in relatively insoluble. Such liposomes can be formed following the procedure described above in Section IIA, where a dried lipid film is hydrated with the aqueous phase at the desired, first pH.

After liposome formation, the external phase of the liposomes is adjusted, by titration, dialysis or the like, to a second pH where the compound to be loaded is relatively water soluble.

The compound to be entrapped in now added to the liposome dispersion, under conditions that allow uptake of the compound by the liposomes to a compound concentration that is several times that of the compound in the bulk medium, as evidenced by the formation of precipitate in the liposomes. Typical incubation temperatures and times follow those given in Section IIA above. At the end of this incubation step, the suspension may be further treated to remove free compound, also as above.

In addition, the pH of the bulk-phase suspension may be adjusted to a pH at or near the internal liposome pH. As noted above, this processing step is particularly useful if the internal pH is in the range from about 5.5 to 8.5, so that the final suspension has a physiological pH.

C. Compound Loading by Charged, Non-Polymeric Species

In accordance with the invention, a suspension of liposomes having an ionizable compound stably encapsulated in the liposomes in precipitated form can also be prepared with multivalent, ionically charged organic compounds as precipitating agents, whether polymeric or non-polymeric in nature.

In practicing the method, there is first prepared a dispersion of liposomes contained in a bulk-phase aqueous medium, and having (i) a higher inside/lower outside gradient of a multivalent, charged precipitating agent, and (ii) substantially no inside-to-outside pH gradient.

Exemplary candidates for precipitating agents include phosphate, pyrophosphate, oligophosphates, fulfate, carbonate, tartrate, oxalate, citrate, nitrilotriacetate, ethylenediamine tetraacetate, dithylenetriamine pentaacetate, maleate, succinate, glutarate, 1,1,-bis(2-hydroxy 3-carboxynaphtyl)methane (pamoate)), as negatively charged agents used in combination with a cationic ionizable compound. For a compound that is ionizable to a negatively charged species, the agent is a multivalent basic species, such as spermine, spermidine and their quaternized derivatives, N,N-bis(benzyl) ethylenediamine (benzathine), and procaine. It is appreciated that, in some instances, a precipitating agent within the invention may be a non-valent acid, or base, that forms a precipitate with a compound to be loaded into the liposome, under the loading conditions (pH, temperature). One such precipitating agent, as an example, is Reinacke salt, especially when the compound is an organic amine.

To identify a suitable precipitating agent, for a selected ionizable compound, the compound is added to a solution of a test agent, similar to the approach used to identify suitable charged polymer agents described above in subsection IIA. Agents that show strong precipitation, at suitable compound and agent concentrations are suitable coprecipitating pairs for use in the invention. On the contrary, the agents which are not precipitating agents for the compound cause very little compound loading (see examples 7–9).

One exemplary pair, for use in the invention, is doxorubicing or one of its derivatives, as a cationic ionizable compound, and an anion of phosphate, sulfate, citrate, tartrate, diethylenetramine pentoacetate, or polyacrylate. Another exemplary pair is penicillin or one of its derivatives, as a negatively charged compound, and benzathine, as a positively charged precipitating agent.

Liposomes having an inside/outside gradient of the precipitating agent are prepared as in IIA above. The liposome dispersion is then incubated with the compound to be encapsulated, under conditions that allow uptake of the compound into liposomes, also as described above. The final product may be further treated to remove free compound.

III. Examples

The following examples illustrate, but in no way are intended to limit, the present invention.

EXAMPLE 1

Liposomes Loaded with Doxorubicin 21.6 mg of polyacrylic acid (molecular weight 2,000; Aldrich Corporation, Milwaukee, Wis.) were dissolved in 3 ml of water and neutralized to pH 7.4 with NaOH to produce 100 milli-eq/L sodium polyacrylate solution. 10 mg of the mixture of egg PC, cholesterol, and PEG (molecular weight 2,000)-DSPE (Avanti Polar Lipids, Birmingham, Ala.) in the molar ratio of 10:5:1 was dissolved in chloroform, the solvent was evaporated in vacuum, the lipid film was incubated with shaking in 1 ml of the above polyacrylate solution, and the lipid dispersion was extruded under pressure through 2 stacked Nucleopore (Pleasanton, Calif.) membranes with pore size 0.2 $\mu$mol. The outer buffer was exchanged for NaCl 0.1 M containing 5 mM of sodium hydroxyethylpiperazine-ethane sulfonate (HEPES) at pH 7.4 using gel chromatography on Sepharose CL-4B (Pharmacia, Piscataway, N.J.); at the same time, unentrapped sodium polyacrylate was also removed. To the so obtained liposomes, doxorubicin (Cetus Oncology, Norwalk, Conn.) was added at 200 nmol/$\mu$mol, of liposomal phospholipid. The mixture was incubated overnight at 37° C. with shaking, treated with Dowex 50W×4 (Sigma Chemical Co., St. Louis, Mo.), and equilibrated with NaCl-HEPES solution to remove non-encapsulated doxorubicin. The resulting liposomes were sterilized by filtration through a 0.2 $\mu$mol filter and assayed for doxorubicin by spectrophotometry and liposomal phospholipid by acid digestion-molybdene blue assay. Doxorubicin content was 129 nmol/ $\mu$mol of liposomal phospholipid. Under similar conditions, doxorubicin loading into liposomes without entrapped sodium polyacrylate was 8 nmol/$\mu$mol of phospholipid.

EXAMPLE 2

Cytotoxicity of Liposomal Doxorubicin

Human nasopharyngeal epidermoid carcinoma (KB) cells were from American Type Culture Collection (ATCC, Rockville, M.D.). The cells were grown in RPMI 1640 medium supplemented with 10% heat inactivated fetal calf serum, harvested by trypsinization, and plated in 96-well tissue culture plates at $2\times10^4$ cells/well. After a 24 hour acclimation period, a solution of free doxorubicin or the doxorubicin liposomes described in Example 1 were added to the cells to achieve final doxorubicin concentrations of 0.125–8 $\mu$g/ml. "Empty" liposomes were added to control cells at matching concentrations of the lipid. After a 96 hour incubation period, viability of the cells was measured by tetrazolium assay (Carmichael, et al., 1987). 50% growth inhibitory concentrations ($IC_{50}$) of the studied preparation were as follows:

| | |
|---|---|
| Free doxorubicin | 0.35 $\mu$g/ml |
| Liposomal doxorubicin | 0.65 $\mu$g/ml |
| "Empty" liposomes | No growth inhibition detected |

EXAMPLE 3

Loading of Doxorubicin into Liposomes with Entrapped Sodium Salt of Chondroitin Sulfate A Liposomes were prepared as in Example 1, except that inner buffer, instead of polyacrylic acid, contained 5 mg/ml of chondroitinsulfate A (Sigma Chemical Co., St. Louis, Mo.). After overnight incubation with doxorubicin (100 mol/μmol of phospholipid) at pH 7.2, free drug was removed from the liposomes, and the liposomes were assayed as in Example 1. The doxorubicin content in the resulting liposomes was 26.0 nmol/μmol of phospholipid.

EXAMPLE 4

Loading of Doxorubicin into Liposomes with Entrapped Sodium Salts of Sulfuric, Phosphoric, Polyvinylsulfuric, or Polyphosphoric Acid Liposomes were prepared from egg phosphatidylcholine using the procedure identical to Example 1 but instead of polyacrylic acid, the inner buffers contained one of the following salts: sodium sulfate, sodium phosphate, sodium polyvinylsulfate (Fluka, Ronkonkoma, N.Y.; average chain length n=13), or sodium polyphosphate (Sigma Chemical Co.; average chain length n=13–18), at a concentration of 100 mill-equivalents of sodium/L. The liposomes were incubated with doxorubicin (300 nmol/μmol of phospholipid) overnight, free drug was removed from the liposomes, and the liposomes were assayed as described in Example 1. Drug incorporation into the liposomes was as follows (in nmol/μmol of phospholipid): sodium sulfate, 82.1±0.95; sodium phosphate, 76.8±2.3; sodium polyvinylsulfate, 109.8±0.25; sodium polyphosphate, 85.2±2.2; "blank" liposomes, containing 100 mM sodium chloride, 1.03±0.06.

EXAMPLE 5

Loading of Doxorubicin into the Liposomes with Entrapped Sulfate, Phosphate, Polyvinylsulfate, or Polyphosphate Sodium Salts in the Presence of Nigericin Liposomes were prepared and loading with doxorubicin as in Example 4, except that prior to drug loading, nigericin was added to the liposomes at a concentration of 5 μmol/L. The following drug incorporation (nmol/μmol of phospholipid) was obtained in the liposomes containing: sodium sulfate, 96.5±1.9; sodium phosphate, 271.9±3.8; sodium polyvinylsulfate, 133.7±1.9; sodium polyphosphate, 169.7±2.7. Therefore, permeabilization of the liposome membrane to hydrogen and sodium ions by nigericin did not decrease drug loading.

EXAMPLE 6

Effect of Membrane-Active Ion Carriers on the Loading of Doxorubicin into the Liposome with Entrapped Potassium Polyacrylate The liposomes prepared according to the present invention can be clearly distinguished from similar liposomes prepared by pH gradient, or ammonium ion gradient methods, by the liposomal response to membrane-active ion carriers which destroy transmembrane electrochemical gradients. For example, CCCP is a membrane proton carrier which destroys transmembrane pH gradients and leads to quick release of a liposomal-entrapped compound. Nigericin, a membrane carrier for protons and monovalent ions, quickly releases doxorubicin from liposomes loaded by the ammonium ion method (Haran, et al., 1993).

In contrast, liposomes prepared according to this invention, load doxorubicin in the presence of CCCP or nigericin with nearly the same efficiency as in the absence of such membrane-active ion carriers. This is shown in FIG. 1, where the loading of doxorubicin into liposomes in the presence of valinomycin, CCCP or nigericin was determined as a function of time. The liposomes were prepared as described in Example 1 to have entrapped potassium polyacrylate. The figure shows that doxorubicin is loaded with substantially equal efficiency in the absence of a membrane-active carriers (•) and in the presence of valinomycin (•), CCCP (∇) or nigericin (▽).

EXAMPLE 7

Loading of Doxorubicin into the Liposomes Containing Ammonium Salt of Polyacrylic or Sulfuric Acids in the Absence of Ammonium Ion Gradient Liposomes with entrapped ammonium sulfate or ammonium polyacrylate were prepared from the lipid mixture of hydrogenated soybean phosphatidylcholine (Avanti PolarLipids, Ala., U.S.A.), cholesterol (Calbiochem, USA), and poly(ethylene glycol) (Mol. weight 2,000) derivative of distearoyl phosphatidyl ethanolamine (PEG-DSPE) (Sygena, Switzerland), at the molar ratio 60:40:6, by lipid film hydration, repetitive freezing-thawing at 60° C. (6 times) and extrusion through two stacked polycarbonate track-etched membranes with the pore size 100 nm at 60° C. (12 times). The bulk aqueous phase of the liposomes was exchanged by gel-filtration for the outer buffer, 0.2 M ammonium chloride, adjusted (when necessary) to pH 7.3 and buffered with 10 mM sodium hydroxyethylpiperazinoethane sulfonate (HEPES). The inner (entrapped) solution had ammonium ion concentration of 200 milli-eqivalent/L, i.e. the same as the outer buffer (no ammonium ion gradient), and the anion composition and pH as indicated below. Polyacrylic acid with mol. weight of 2,000 (Aldrich Chemical Co.) was used. Doxorubicin was added to the liposomes at 2 mg for each 6–8 micro-mol of phospholipid, and incubated with shaking at 60° C., i.e. above the transition temperature of the lipid bilayer, for various times as specified below. At this temperature, doxorubicin did not form a detectable precipitate in the presence of sulfate anion, but was visibly precipitated by a polyacrylate anion. Doxorubicin-loaded liposomes were separated from the free drug by gel-chromatography on Sephadex G-75, eluted with the outer buffer. Liposomal doxorubicin was assayed by spectrophotometry at 485 nm, phospholipid was quantitated by molybdate method after acid digestion of the liposomes. The following results were obtained:

| Inner Buffer | Outer Buffer | Loading time | Doxorubicin incorporation into liposomes, mg of drug/mmol of liposome phospholipid |
| --- | --- | --- | --- |
| $SO_4^{2-}$, pH 7.3 | Cl—, pH 7.3 | 1 hour | 6.1 ± 0.8 |
| $SO_4^{2-}$, pH 7.3 | Cl—, pH 7.3 | 16 hours | 5.1 ± 0.2 |
| Polyacrylate, pH 5.2 | Cl—, pH 5.2 | 1 hour | 59.7 ± 2.5 |
| Polyacrylate, pH 7.3 | Cl—, pH 7.3 | 1 hour | 91.0 ± 2.8 |

Thus, liposomes containing ammonium sulfate at 60° C. in the absence of ammonium ion gradient absorbed very small amounts of doxorubicin, while the liposomes containing ammonium polyacrylate absorbed considerable amounts of doxorubicin even without ammonium ion gradient.

EXAMPLE 8

Loading of Doxorubicin into Liposomes with Entrapped Anions and Essentially Free from Transmembrane pH or Ammonium Ion Gradients Aqueous solutions containing ammonium salts of hydrochloric, nitric, methanesulfonic, L(+)-tartaric, citric, sulfuric, phosphoric, diethylenetriamine pentaacetic (DTPA), or polyacrylic (Mol. weight. 2,000) acids were prepared by titration of the respective acids in water with the standard aqueous solution of ammonium hydroxide to achieve pH 7.3±0.05, followed by volume adjustment to achieve 0.2 equivalent/L of ammonium ion, and, if necessary, by addition of dry sucrose to achieve osmolarity of 377 mmol/kg. (These solutions are hereinafter referred to as Inner Buffers). All solutions additionally contained 10 mM hydroxyethylpiperazinoethane sulfonic acid (HEPES) to stabilize the pH at titration endpoint. To afford determination of intraliposomal pH, a fluorescence indicator 8-hydroxypyrene trisulfonate was added to the solutions to the final concentration of 0.2 mM. Liposomes containing entrapped ammonium salt solutions as above were prepared from egg phosphatidyl choline, cholesterol, and PEG-DSPE as described in the Example 7, except that lipid hydration and extrusion were carried out at room temperature. The bulk aqueous phases of liposome preparations were exchanged by gel-filtration for an aqueous solution (Outer buffer) containing 0.2 M ammonium chloride, 10 mM HEPES, pH 7.3, osmolarity 377 mmol/kg, to obtain liposome preparations substantially without transmembrane ammonium-ion gradients. Loading of doxorubicin was performed as in Example 7, except that it was at 36° C. for 12 hours. Intraliposomal pH was determined using HPTS fluorescence method (Straubinger, et al., 1990) prior to drug loading, and indicated essentially no inside-outside pH gradient (less than 0.2 pH units), compared with the gradient of several pH units typical for ammonium ion gradient liposomes (Haran, et al., 1993). The following results were obtained (nd, not determined)

| Inner Buffer anion composition | pH gradient, inside vs. outside. | Doxorubicin incorporation into liposomes, mg of drug/mmol of liposome phospholipid |
|---|---|---|
| chloride | −0.11 | 16.8 |
| nitrate | −0.16 | 12.4 |
| methanesulfonate | −0.21 | 17.1 |
| L(+)–tartrate | nd | 27.5 |
| sulfate | nd | 33.5 |
| DTPA | nd | 40.8 |
| phosphate | nd | 68.1 |
| citrate | −0.13 | 97.9 |
| polyacrylate | −0.02 | 142.7 |

Thus, "active loading" of doxorubicin was achieved in the liposomes containing organic or inorganic non-polymeric anions and essentially free from transmembrane pH- or ammonium ion gradients.

EXAMPLE 9

Correlation between the Drug Precipitation by the Inner Buffer Anions and the Extent of Doxorubicin Loading into Liposomes with Entrapped Anions and Essentially Free From Transmembrane pH or Ammonium Ion Gradients Doxorubicin hydrochloride was added to the aliquots of Inner Buffers described in the Example 8 above to achieve final concentration of 1 mg/ml. The mixtures were briefly incubated at 60° C. to effect maximum drug dissolution, and further equilibrated at ambient temperature (22° C.) with gentle shaking for 3 hours. Precipitated doxorubicin was separated by centrifugation of an Eppendorf centrifuge (10,000 rpm, 5 min.), and the amount of doxorubicin in supernatant fluid was determined by spectrophotometry. The percent of drug precipitation was calculated as 100% less the percent of doxorubicin remaining in the supernatant fluid relative to the total added doxorubicin.

The following results were obtained:

| Inner Buffer anion composition | Doxorubicin precipitation, % |
|---|---|
| chloride | 1.1 |
| nitrate | 0 |
| methanesulfonate | 0 |
| L(+)-tartrate | 25.0 |
| sulfate | 47.5 |
| DTPA | 58.1 |
| phosphate | 73.7 |
| citrate | 81.4 |
| polyacrylate | 98.4 |

It is apparent from the comparison with the data of Example 8 that doxorubicin loading in the absence of pH- or ammonium-ion gradient was effected when the liposome-entrapped anions, whether polymeric or non-polymeric, were capable of precipitating the drag. Using Student's t-test, statistically significant correlation was found between the extent of drug loading into the liposome and the drug solubility in the Inner Buffer (correlation coefficient R=0.9043; probability of null hypothesis p<0.0005).

It is claimed:

1. A method for producing liposome-encapsulated compounds, comprising:
   incubating a compound with a suspension of liposomes in a medium, said liposomes spatially defined by a membrane surrounding an interior, and said compound capable of having a charge sign, and
   said liposomes comprising within the interior a concentration of compound-precipitating ion, wherein said concentration of said compound-precipitating ion is greater in the interior of the liposomes compared to said medium, and is sufficient to effect precipitation of said compound within said liposome interior during incubation; and
   said liposomes having, prior to precipitation, substantially no transmembrane gradient of a hydrogen ion; and
   said liposomes having, prior to precipitation, substantially no transmembrane gradient of an ammonium ion; and
   said liposomes having, prior to precipitation, substantially no transmembrane gradient of a membrane-permeating ion having the same charge sign as said compound.

2. A method of claim 1, wherein the medium is substantially free of compound-precipitating ion.

3. A method of claim 1, wherein the compound is ionizable in said medium to a positive charge.

4. A composition of claim 3, wherein the compound-precipitating ion is a polymeric anion.

5. A method of claim 3, wherein the compound-precipitating ion is a multivalent non-polymeric acid.

6. A method of claim 1, wherein the compound is doxorubicin, or an analog thereof.

7. A method of claim 3, wherein the compound-precipitating ion is selected from the group consisting of:

polyacrylate; chondroitin sulfate A; polyvinylsulfate; polyphosphorate; phosphate; pyrophosphate; sulfate; citrate; tartarate; nitrilotiacetate; ethylenediamine tetraacetate; and diethylenetriamine pentaacetate.

8. A method of claim 1, wherein the compound is ionizable in said medium to a negative charge.

9. A method of claim 8, wherein the compound-precipitating agent is a polymeric cation.

10. A composition of claim 8, wherein the compound-precipitating agent is a multivalent non-polymeric cation.

11. A method of claim 1, wherein the compound is penicillin, or an analog thereof.

12. A method of claim 11, wherein the multivalent non-polymeric cation is a benzathine cation.

13. A liposome composition formed by incubation of compound with a suspension of liposomes comprising:

liposomes in a medium, said liposomes spatially defined by a membrane surrounding an interior, and said compound capable of having a charge sign; and wherein the compound is in the form of a precipitating ion-induced precipitate; and said liposomes comprising a concentration of a compound-precipitating ion which is greater in the liposome interior compared to said medium; and said liposomes having prior to formation of said precipitate, substantially no transmembrane gradient of a hydrogen ion; and said liposomes having, prior to formation of said precipitate, substantially no transmembrane gradient of an ammonium ion; and said liposomes having, prior to formation of said precipitate, substantially no transmembrane gradient of a membrane-permeating ion having the same charge sign as said compound.

14. A liposome composition of claim 13, wherein the medium is substantially free of said compound-precipitating ion.

15. A liposome composition of claim 13, wherein the compound is ionizable in said medium to a positive charge.

16. A liposome composition of claim 13, wherein the compound-precipitating ion is a polymeric anion.

17. A liposome composition of claim 13, wherein the compound-precipitating ion is a multivalent non-polymeric anion.

18. A liposome composition of claim 13, wherein the compound is doxorubicin, or an analog thereof.

19. A liposome composition of claim 13, wherein the compound-precipitating ion is selected from the group consisting of: polyacrylate; chondroitin sulfate A; polyvinylsulfate; polyphosphorate; phosphate; pyrophosphate; sulfate; citrate; tartarate; nitrilotiacetate; ethylenediamine tetraacetate; and diethylenetriamine pentaacetate.

20. A liposome composition of claim 13, wherein the compound is ionizable in said medium to a negative charge.

21. A liposome composition of claim 13, wherein the compound-precipitating ion is a polymeric cation.

22. A liposome composition of claim 13, wherein the compound-precipitating ion is a multivalent non-polymeric cation.

23. A liposome composition of claim 22, wherein the compound is penicillin, or an analog thereof.

24. A liposome composition of claim 22, wherein the multivalent non-polymeric cation is a benzathine cation.

* * * * *